United States Patent [19]

Rouy

[11] 4,336,390

[45] Jun. 22, 1982

[54] BENZOXAZOLONE PREPARATION

[75] Inventor: Noël Rouy, Lesigny, France

[73] Assignee: Rhone-Poulenc Agrochimie, Lyons, France

[21] Appl. No.: 158,494

[22] Filed: Jun. 11, 1980

[30] Foreign Application Priority Data

Jun. 20, 1979 [FR] France .................................. 79 16334

[51] Int. Cl.³ ............................................ C07D 263/58
[52] U.S. Cl. ..................................................... 548/221
[58] Field of Search ........................................... 548/221

[56] References Cited

FOREIGN PATENT DOCUMENTS 2051782  1/1981  United Kingdom ................. 548/221

OTHER PUBLICATIONS

Arcus, et al., "J. of the Chemical Society" (London) (1953), pp. 1937–1940.
Graebe, et al., "Ber." (1902), pp. 2747–2752.

Primary Examiner—Anton H. Sutto
Attorney, Agent, or Firm—Burns, Doane, Swecker & Mathis

[57] ABSTRACT

Benzoxazolone is prepared by reacting salicylamide with an alkali metal hypochlorite in an aqueous reaction medium comprising an alkali metal hydroxide, the alkali metals comprising said hypochlorite and said hydroxide necessarily including both sodium ions and potassium ions.

16 Claims, No Drawings

BENZOXAZOLONE PREPARATION

CROSS-REFERENCE TO RELATED APPLICATIONS

Copending applications, Ser. Nos. 143,857 and 143,859, both filed Apr. 25, 1980, and assigned to the assignee hereof.

BACKGROUND OF THE INVENTION

1. Field of the Invention:

The present invention relates to a process for the preparation of benzoxazolone from salicylamide, and more especially, to the preparation of benzoxazolone from salicylamide and hypochlorite ions, in an aqueous reaction medium comprising hydroxyl, and both sodium and potassium ions.

2. Description of the Prior Art:

Benzoxazolone is a known compound having the structural formula:

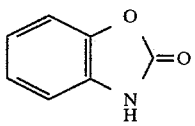

(I)

Such known compound is a useful intermediate in the synthesis of a variety of other materials, e.g., the insecticide phosalone. And benzoxazolone is ofttimes designated benzoxazolinone, in particular in the English speaking countries.

Salicylamide has the structural formula:

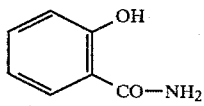

Benzoxazolone was first prepared from salicylamide in 1902 (Graebe and Rostovzeff, Ber., 35, page 2,747). In accordance with this process, hypochlorite, in the presence of sodium hydroxide, is reacted with salicylamide. Fifty years later (Arcus and Greenwood, *J. Chem. Soc.*, 1953, pages 1,937–1,940), the same process was confirmed, it being noted that high concentrations of the alkaline agent afforded better results than low concentrations. Nevertheless, the known process remains deficient in terms of the yields attainable, as well as control over the reaction medium.

SUMMARY OF THE INVENTION

Accordingly, a major object of the present invention is the provision of an improved process for preparing benzoxazolone from salicylamide in improved yields.

Another object of the present invention is the provision of an improved process for preparing benzoxazolone from salicylamide utilizing a relatively concentrated reaction medium, such as to avoid the necessity of conducting the reaction with excessively large amounts of dilute reaction mixture.

Yet another object of the invention is to provide for the preparation of benzoxazolone from a relatively fluid reaction medium, such that said reaction medium can readily be stirred and homogenized in satisfactory manner.

Other objects, features and advantages of the invention will become more apparent from the description which follows.

Briefly, the present invention features the preparation of benzoxazolone from salicylamide, which process comprises reacting salicylamide with hypochlorite ions, in the presence of water and of additonal hydroxyl ions, and both sodium ions and potassium ions.

DETAILED DESCRIPTION OF THE INVENTION

More particularly, the topic reaction sequence can conveniently be represented as follows:

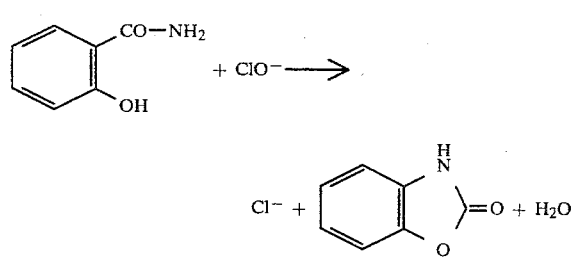

The concentration of hypochlorite ions in the aqueous reaction medium is advantageously between about 0.05 and 3 g. ions/liter, preferably between about 0.1 and 1.5 g ions/liter.

The concentration of additional hydroxyl ions in the aqueous reaction medium is advantageously between about 1.5 and 8 g. ions/liter, preferably between about 2.5 and 6 g. ions/liter.

The concentration of salicylamide in the aqueous reaction medium is advantageously between about 0.2 and 4 mols/liter, preferably between about 0.5 and 3 mols/liter.

The ratio of the number of $Na^+$ to $K^+$ ions present is advantageously such that the ratio of the molar concentrations of $Na^+$ to $K^+$ ions, i.e., $Na^+/K^+$, is between about 0.1 and 2, preferably between about 0.3 and 1.5.

The reaction temperature is typically between about 0° and 50° C., preferably between about 10° and 30° C.

A convenient method for carrying out the reaction according to the invention comprises mixing an aqueous solution of alkali metal hypochlorite with a solution of salicylamide in an alkali metal hydroxide.

For example, sodium hypochlorite or potassium hypochlorite can be used; as regards the solution of salicylamide in an alkali metal hydroxide, same can be a solution in sodium hydroxide (NaOH) or potassium hydroxide (KOH), but, in a preferred embodiment of the invention, an aqueous solution of sodium hypochlorite is mixed with an aqueous solution of salicylamide containing potassium hydroxide.

Upon completion of the reaction, the benzoxazolone formed is isolated by any means which is in and of itself known. Thus, usually, the excess hypochlorite is consumed by a reducing agent and the reaction medium (which is heated, if appropriate, in order to be rendered more fluid) is then neutralized. After neutralization, the benzoxazolone precipitates and can be collected by filtration, or draining, or any other equivalent means.

The salicylamide employed as a reactant in the present invention is a known, readily commercially available material; same can be utilized as such, in its isolated form, or also in the form of a solution, or simply as crude product.

It too will be appreciated that, in the foregoing description of the invention, it has generally been set forth that the subject process comprises the reaction of salicylamide because such material is most conveniently employed; however, in reality, under the conditions of reaction, or even prior to its introduction into the reaction mixture, the salicylamide can be in the form of an alkali metal salt or alkali metal phenate thereof; thus, it is intended herein and in the claims which follow, that by "salicylamide" there is intended both the free base as well as the phenate thereof.

In order to further illustrate the present invention and the advantages thereof, the following specific examples are given, it being understood that same are intended only as illustrative and in nowise limitative.

EXAMPLE 1

An aqueous solution containing 2.17 mols/liter of sodium hypochlorite and 2.2 mols/liter of sodium chloride (505 cc) was added gradually, over the course of 75 minutes, to an aqueous solution containing 3.0 mols/liter of salicylamide and 9.3 mols/liter of potassium hydroxide (330 cc).

The mixture was stirred at 28° C. throughout the addition and for an additional 120 minutes after such addition was completed. Sodium sulfite, $Na_2SO_3$, (8 g, 0.064 mol) was then added in order to consume the excess hypochlorite.

An aqueous solution containing 7.1 mols/liter of sulfuric acid (230 cc) was then added, while at the same time heating the mixture at 70° C. and under stirring. The mixture was cooled to 40° C. and then filtered.

The precipitate of benzoxazolone was washed with water. The benzoxazolone was thus obtained in a yield of 96%, relative to the starting material salicylamide.

EXAMPLE 2

Example 1 was repeated, but with the following modifications:

An aqueous solution containing 2.10 mols/liter of sodium hypochlorite and 2.2 mols/liter of sodium chloride (525 cc) is added gradually, over the course of 90 minutes, to an aqueous solution containing 3.0 mols/liter of salicylamide and 9.3 mols/liter of potassium hydroxide (330 cc).

The mixture was stirred at 10° C. throughout the addition and for an additional 120 minutes after such addition was completed.

Sodium sulfite (11 g. 0.087 mol) was added. An aqueous solution containing 11.5 mols/liter of hydrochloric acid (280 cc) was then added, under stirring at 25° C.

The mixture was filtered at ambient temperature. The precipitate of benzoxazolone was washed with water. The benzoxazolone was obtained in a yield of 95%.

COMPARATIVE EXAMPLES 3 AND 4

Examples 1 and 2 were repeated, except that either $Na^+$ derivatives alone, or $K^+$ derivatives alone, were utilized. The respective reaction media became very difficult to stir as a result of the formation of copious salt precipitates, and necessitated considerable dilution with water; moreover, copious foams were also formed and these too considerably hampered the progress of the reaction.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of benzoxazolone, which comprises reacting salicylamide, a free base of salicylamide or an alkali metal phenate of salicylamide, with an alkali metal hypochlorite in an aqueous reaction medium comprising an alkali metal hydroxide, the alkali metals comprising said hypochlorite and said hydroxide including both sodium ions and potassium ions, and with the amount of sodium and potassium ions present being sufficient to effectively maintain a readily stirrable and homogenizable reaction medium.

2. The process as defined by claim 1, wherein the ratio of the molar concentration of $Na^+$ ions to $K^+$ ions ranges from about 0.1 to 2.

3. The process as defined by claim 2, wherein said ratio ranges from about 0.3 to 1.5.

4. The process as defined by claims 2 or 3, wherein the concentration of hypochlorite ions in the aqueous reaction medium ranges from about 0.05 to 3 g. ions/liter.

5. The process as defined by claim 4, wherein said hypochlorite concentration ranges from about 0.1 to 1.5 g. ions/liter.

6. The process as defined by claim 4, wherein the concentration of hydroxyl ions in the aqueous reaction medium ranges from about 1.5 to 8 g. ions/liter.

7. The process as defined by claim 6, wherein said hydroxyl ion concentration ranges from about 2.5 to 6 g. ions/liter.

8. The process as defined by claim 6, wherein the concentration of salicylamide in the aqueous reaction medium ranges from about 0.2 to 4 mols/liter.

9. The process as defined by claim 8, wherein said salicylamide concentration ranges from about 0.5 to 2 mols/liter.

10. The process as defined by claim 8, wherein the temperature of the reaction medium ranges from about 0° to 50° C.

11. The process as defined by claim 10, said temperature ranging from about 10° to 30° C.

12. The process as defined by claim 8, said reaction medium comprising an aqueous solution of the alkai metal hypochlorite and a solution of the salicylamide in the alkali metal hydroxide.

13. The process as defined by claim 12, said reaction medium comprising an aqueous solution of sodium hypochlorite mixed with an aqueous solution of salicylamide and potassium hydroxide.

14. The process as defined by claim 8, the salicylamide comprising an alkali metal phenate thereof.

15. The process as defined by claim 8, the salicylamide comprising free base salicylamide.

16. The process as defined by claim 8, further comprising, upon completion of the reaction, reducing the unreacted hypochlorite.

* * * * *